US00PP26082P3

(12) United States Plant Patent
Meilland

(10) Patent No.: US PP26,082 P3
(45) Date of Patent: Nov. 17, 2015

(54) FLORIBUNDA ROSE PLANT NAMED 'MEITALREA'

(50) Latin Name: *Rosa hybrida*
Varietal Denomination: cv. Meitalrea

(71) Applicant: CP DELAWARE, INC., Wilmington, DE (US)

(72) Inventor: Alain A. Meilland, Antibes (FR)

(73) Assignee: CP DELAWARE, INC., Wilmington, DE (US)

( * ) Notice: Subject to any disclaimer, the term of this patent is extended or adjusted under 35 U.S.C. 154(b) by 32 days.

(21) Appl. No.: 13/987,569

(22) Filed: Aug. 8, 2013

(65) Prior Publication Data

US 2015/0047081 P1 Feb. 12, 2015

(51) Int. Cl.
*A01H 5/02* (2006.01)

(52) U.S. Cl.
USPC ..... Plt./143
CPC ..... *A01H 5/0222* (2013.01)

(58) Field of Classification Search
USPC ..... Plt./143
CPC ..... A01H 5/0222
See application file for complete search history.

*Primary Examiner* — Keith O. Robinson
(74) *Attorney, Agent, or Firm* — Buchanan, Ingersoll & Rooney PC

(57) ABSTRACT

A new and distinct variety of Floribunda rose plant is provided that abundantly and substantially continuously forms attractive single cup-shaped blossoms displaying at opening an irregular blend of yellow and luminous red which evolves to a greater concentration of red at maturity. The vegetation is strong. A bushy growth habit is displayed. The foliage is dense dark green with a glossy upper surface. The tolerance to disease is good, with a light sensitivity to black spot having been observed during observations to date. The plant is well suited for providing distinctive attractive ornamentation in the landscape.

1 Drawing Sheet

Botanical/commercial classification: *Rosa hybrida*/Floribunda Rose Plant.

Varietal denomination: cv. Meitalrea.

SUMMARY OF THE INVENTION

The new variety of *Rosa hybrida* Floribunda rose plant was created in France by artificial pollination wherein two parents were crossed which previously had been studied in the hope that they would contribute the desired characteristics. The female parent (i.e., the seed parent) was an unnamed and unreleased seedling (non-patented). The male parent (i.e., pollen parent) additionally was an unnamed and unreleased seedling (non-patented).

The parentage of the new variety can be summarized as follows:

Unnamed Seedling×Unnamed Seedling.

The seeds resulting from the above pollination were sown and small plants were obtained which were physically and biologically different from each other. Selective study resulted in the identification of a single plant of the new variety.

It was found that the new Floribunda rose plant of the present invention:

(a) forms strong vegetation, (b) exhibits a bushy growth habit with dense dark green foliage having a glossy upper surface, (c) abundantly and substantially continuously forms attractive single cup-shaped blossoms displaying at opening an irregular blend of yellow and luminous red which evolves to a greater concentration of red with maturity, and (d) is well suited for providing distinctive attractive ornamentation in the landscape.

The tolerance to disease is good with a light sensitivity to black spot (i.e., *Diplocarpon rosae*), sometimes known as Marsonia, having been observed during observations to date.

The new variety of the present invention can be readily distinguished from its ancestors. More specifically, the female parent displays a dusted ochre blossom coloration, and the male parent displays an ochre streaked with yellow blossom coloration.

The new variety also can be readily distinguished from the 'Meisiastri' variety (U.S. Plant Pat. No. 20,719) and the 'Radfifth' variety (U.S. Plant Pat. No. 22,316). More specifically, the 'Meisiastri' variety forms dissimilar blossoms that are coral in coloration with substantial cream-to-yellow striping, and the 'Radfifth' variety displays a dissimilar upright and climbing growth habit.

The new variety well meets the needs of the horticultural industry and can be grown to advantage as colorful ornamentation in parks and gardens.

The new variety has been found to undergo asexual propagation at Le Cannet des Maures, Var, France, by a number of routes, including budding, grafting, and the use of cuttings. Such asexual propagation by the above-mentioned techniques has shown that the characteristics of the new variety are stable and are strictly transmissible by such asexual propagation from one generation to another. Accordingly, the new variety undergoes asexual propagation in a true-to-type manner.

The new variety has been named 'Meitalrea'.

BRIEF DESCRIPTION OF THE PHOTOGRAPH

The accompanying photograph shows as nearly true as it is reasonably possible to make the same in a color illustration of this character, typical specimens of plant parts of the new variety. The rose plants of the new variety were approximately two years of age and were observed during July while budded on *Rosa laxa* rootstock and growing outdoors at Le Cannet des Maures, Var, France.

DETAILED BOTANICAL DESCRIPTION

Figures 1, 2, 3, 4, 5, 6, 7, 8, 9, 10, 11, 12, 13, 14, 15, 16, 17:
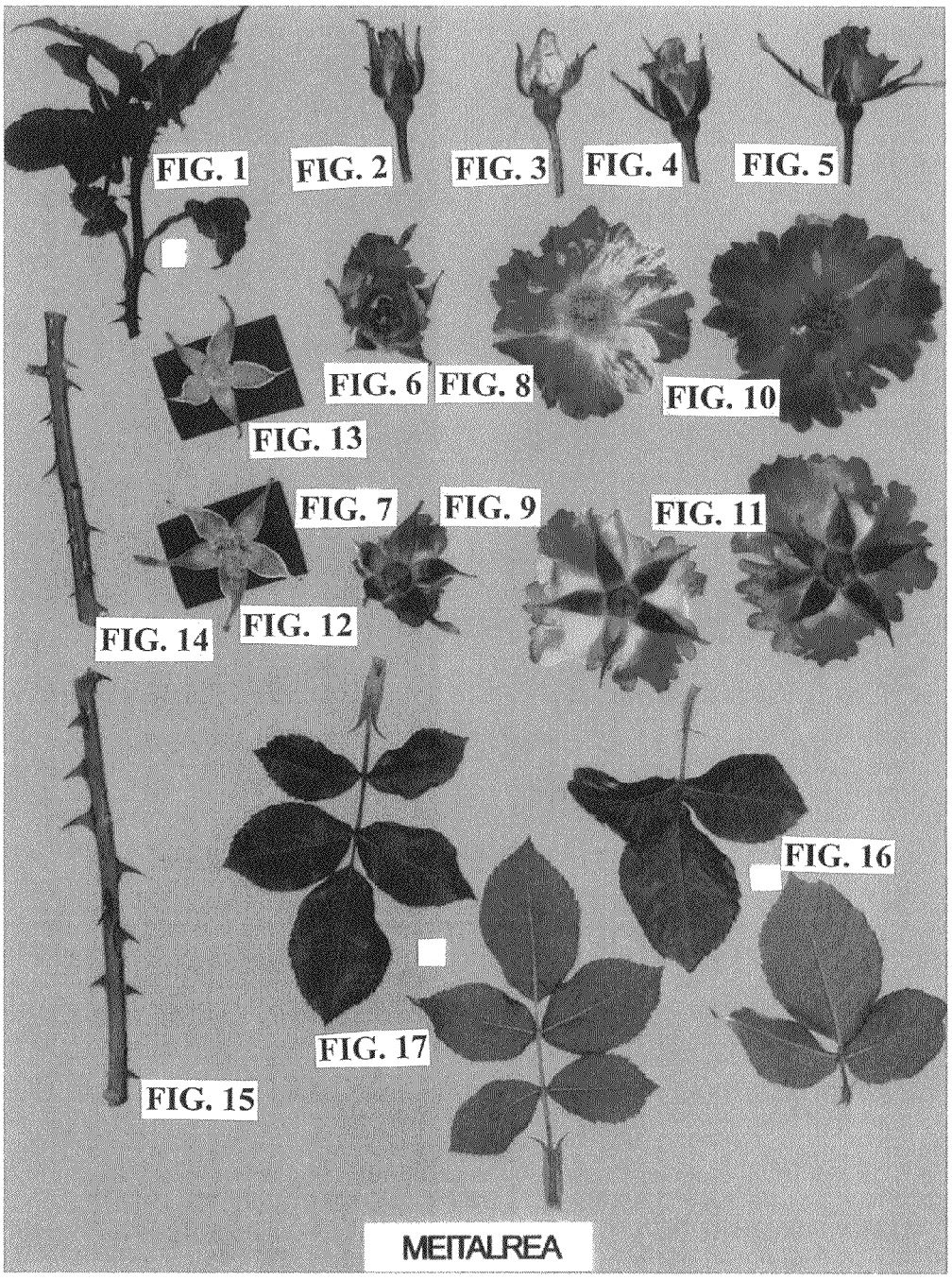
FIG. 1 illustrates a specimen of a young shoot.
FIG. 2 illustrates a specimen of a floral bud at the opening of the sepals.
FIG. 3 illustrates a specimen of a floral bud at the further opening of the sepals.
FIG. 4 illustrates a specimen of a floral bud at the opening of the petals.
FIG. 5 illustrates a specimen of a flower as opening begins.
FIG. 6 illustrates a specimen of a flower in the course of opening—plan view—obverse.
FIG. 7 illustrates a specimen of a flower in the course of opening—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of an open flower at full maturity—plan view—obverse.
FIG. 11 illustrates a specimen of an open flower at full maturity—plan view—reverse.
FIG. 12 illustrates a specimen of a floral receptacle showing arrangement of the stamens and pistils.
FIG. 13 illustrates a specimen of a floral receptacle showing arrangement of the pistils (stamens removed)
FIG. 14 illustrates a specimen of a flowering stem.
FIG. 15 illustrates a specimen of a main branch.
FIG. 16 illustrates a specimen of a pair of leaves with 3 leaflets—plan view—upper surface (upper left), and—under surface (lower right)
FIG. 17 illustrates a specimens of a pair of leaves with 5 leaflets—plan view—upper surface (upper left), and—under surface (lower right).

The chart used in the identification of the colors is that of The Royal Horticultural Society (R.H.S. Colour Chart—1995) except where ordinary color terms are utilized. Common color terms are to be accorded their customary dictionary significance. The description is based upon the observation of plants of the new variety at an age of approximately two years during the month of May while being grown outdoors while budded on *Rosa laxa* rootstock at Le Cannet des Maures, Var, France.

Class: Floribunda.

Plant:

*Growth habit.*—Bushy.

*Height.*—Commonly approximately 60 cm on average.

*Width.*—Commonly approximately 50 cm on average.

Branches:

*Color.*—Young stems: commonly near Yellow-Green Group 146B. Adult wood: commonly near Yellow-Green Group 148A.

*Small thorns.*—Size: commonly approximately 6 mm in length on average with an obovate and narrow base on young stems. Quantity: commonly approximately 3 on average over a length of 10 cm on young stems, and commonly absent on adult stems. Color: commonly near Greyed-Red Group 195A more or less suffused with Greyed-Orange Group 17A on young stems.

*Longer thorns.*—Configuration: very elongated and curved downwards on the upper surface and very concave on the under surface. Size: commonly approximately 8 mm in length on average with an obovate and narrow base on young stems, and commonly 1 cm in length on average with an obovate and narrow base on adult stems. Quantity: commonly approximately 6 on average over a length of 10 cm on young stems, and commonly approximately 5 on average over a length of 10 cm on adult stems. Color: commonly near Greyed-Green Group 195A more or less suffused with near Greyed-Orange Group 174A on young stems, and near Greyed-Purple Group 183C on adult stems.

Leaves:

*Overall appearance.*—Dense dark green.

*Leaflets.*—Shape: generally oval. Number: 3, and most often 5.

*Size.*—Terminal leaflets commonly are approximately 5.3 cm in length on average and approximately 3.4 cm in width on average. Apex: somewhat cuspidate. Base: rounded. Serration: slightly denticulate, small and single. Texture: firm and leathery on the under surface, and glossy on the upper surface. Color (young foliage): near Green Group 137B on the upper surface, and near Yellow-Green Group 146C on the under surface. Color (adult foliage): near Green Group 139A on the upper surface, and near Yellow-Green Group 147B on the under surface.

*Petiole.*—Texture: non-glandular on the upper surface and commonly with many prickles on the under surface. Color: near Yellow-Green Group 146B on the upper surface, and near Yellow-Green Group 146C on the under surface.

*Rachis.*—Color: near Yellow-Green Group 146B on the upper surface, and near Yellow-Green Group 146C on the under surface. Texture: non-glandular on the upper surface and commonly with numerous prickles on the under surface.

*Stipules.*—General appearance: adnate, pectinate, and rather broad. Size: commonly approximately 2.1 cm in length on average, and approximately 5 mm in width on average. Texture: generally smooth on the upper and under surfaces. Color: near Yellow-Green Group 146B on the upper surface, and near Yellow-Green Group 146C on the under surface.

Inflorescence:

*Number of flowers.*—Commonly approximately 2 to 7 blossoms per stem.

*Buds.*—Shape: generally conical and small in size. Length: approximately 1.7 cm on average. Width: approximately 1.2 cm at the widest point on average. Texture: smooth on outer surface of petals. Color: as the calyx breaks: on the upper surface near Yellow Group 12A more or less streaked with near Orange-Red Group 33A and Red Group 45A and with a spot of near Yellow Group 12A at the base, and on the under surface near Yellow Group 12A more or less streaked with Red Group 44C and with a spot of Yellow Group 12A at the base.

*Flower.*—Diameter: approximately 6 to 7 cm on average when fully open. Shape: cup-shaped. Color (in course of opening): upper side: near Yellow Group 12A more or less suffused with Yellow-Orange Group 14A and more or less streaked with Orange-Red Group 33A and with a spot of near Yellow Group 12A at the base. under side: near Yellow Group 12A streaked with Red Group 45D and with a spot of near Yellow Group 12A at the base. Color (when open): upper side: near Yellow Group 12A very amply suffused with near Red Group 44A and more or less streaked with Red Group 45A and with a spot of near Yellow Group 12A at the base. under side: near Yellow Group 12A and amply suffused and streaked with near Red Group 45A and with a spot of near Yellow Group 12A at the base. Fragrance: none. Petal number: commonly approximately 9 or 10 on average under normal growing conditions. Petal shape: commonly display a rounded tip generally with weak incision and an obtuse base. Petal arrangement: imbricated and commonly without petaloids. Petal texture: firm and leathery on both surfaces. Petal length: commonly approximately 3 cm on average. Petal width: commonly approximately 3.1 cm on average. Petal drop: good with the petals commonly detaching cleanly before drying. Stamen number: commonly approximately 116 on average. Anthers: arranged regularly around the styles, commonly approximately 3 mm in size on average, and near Greyed-Orange Group 163B in coloration. Filaments: commonly approximately 5 mm in length on average, and near Yellow Group 9A in coloration. Pistils: commonly approximately 92 on average. Styles: commonly approximately 1 mm in size on average, and near Greyed-Yellow Group 162A in coloration. Stigmas: commonly approximately 5 mm in size and near Greyed-Red Group 180A in coloration.

*Receptacle.*—Length: commonly approximately 9 mm on average. Width: commonly approximately 9 mm on average at widest point. Shape: pitcher-shaped. Texture: smooth. Color: near Yellow-Green Group 144A. Fruit formation: the quantity of fruit and seeds appears to be influenced by the climatic conditions that are encountered. Hips: rounded in configuration and commonly near Orange-Red Group 35B in coloration.

*Sepals.*—Length: commonly approximately 2.5 cm on average. Width: commonly approximately 9 mm on average at the widest point. Shape: longish and narrow and commonly upright upon initial opening. Texture: slightly tomentose on the upper surface and smooth on the under surface. Color: commonly near Yellow-Green Group 146D on the upper surface and near Yellow-Green Group 144A more or less suffused with Greyed-Purple Group 183B on the under surface.

*Peduncle.*—Length: commonly approximately 4.5 cm on average. Width: commonly approximately 4 mm on average. Texture: pubescent. Color: near Yellow-Green Group 144A.

Development:

*Vegetation.*—Strong.

*Blooming.*—Medium season, very abundant and substantially continuous.

*Tolerance to diseases.*—Good, with a light sensitivity to black spot (*Diplocarpon rosae*) having been observed during observations to date.

I claim:

1. A new and distinct Grandiflora rose plant characterized by the following characteristics:

(a) forms strong vegetation, (b) exhibits a bushy growth habit with dense dark green foliage having a glossy upper surface, (c) abundantly and substantially continuously forms attractive single cup-shaped blossoms displaying at opening an irregular blend of yellow and luminous red which evolves to a greater concentration of red with maturity, and (d) is well suited for providing distinctive attractive ornamentation in the landscape;

substantially as shown and described.

* * * * *

MEITALREA